(12) United States Patent
Brini et al.

(10) Patent No.: US 7,623,241 B2
(45) Date of Patent: Nov. 24, 2009

(54) METHOD FOR AUTOMATIC COLOR MATCHING OF TRANSPARENT WOOD STAINS

(75) Inventors: Maurizio Brini, Bologna (IT); Barbara Bartolomei, Bologna (IT)

(73) Assignee: Arch Chemicals, Inc., Norwalk, CT (US)

( * ) Notice: Subject to any disclaimer, the term of this patent is extended or adjusted under 35 U.S.C. 154(b) by 98 days.

(21) Appl. No.: 11/787,990

(22) Filed: Apr. 17, 2007

(65) Prior Publication Data

US 2008/0015791 A1     Jan. 17, 2008

Related U.S. Application Data

(60) Provisional application No. 60/799,921, filed on May 12, 2006.

(51) Int. Cl.
G01N 21/25 (2006.01)
C22C 14/5412 (2006.01)
(52) U.S. Cl. .................. 356/408; 356/319; 427/8; 427/10; 427/258
(58) Field of Classification Search ............ 356/408, 356/319, 402, 421, 425, 300; 427/8, 10, 427/259
See application file for complete search history.

(56) References Cited

U.S. PATENT DOCUMENTS

| 4,887,217 | A | 12/1989 | Sherman et al. |
| 5,933,578 | A | 8/1999 | Van de Capelle et al. |
| 7,466,415 | B2 * | 12/2008 | Gibson et al. ............ 356/402 |
| 2004/0131756 | A1 | 7/2004 | Skierski et al. |

FOREIGN PATENT DOCUMENTS

| WO | 2004048910 A2 | 6/2004 |
| WO | 2004048910 A3 | 6/2004 |
| WO | 2004090488 A1 | 10/2004 |

* cited by examiner

Primary Examiner—L. G Lauchman
(74) Attorney, Agent, or Firm—Dale L. Carlson; Wanli Wu; Wiggin and Dana, LLP

(57) ABSTRACT

A method of producing a finish for a paper substrate, wherein the finish provides the paper substrate with a color that matches the color of a target object. In accordance with the method, calculations are performed to determine the quantities of at least one group of colorants required to produce a semitransparent wood stain from a vehicle, wherein when the semitransparent wood stain is applied to the paper substrate, the paper substrate will have a color that matches the target object. The calculations are performed using reflectance measurements of the target object obtained using a spectrophotometer and previously obtained spectral data of the colorants as applied to a paper substrate. The colorants used to form the transparent or semitransparent wood stain do not include a white colorant or black-and-white masstone.

8 Claims, No Drawings

METHOD FOR AUTOMATIC COLOR MATCHING OF TRANSPARENT WOOD STAINS

CROSS-REFERENCE TO RELATED APPLICATIONS

This application claims the benefit of U.S. Provisional Application No. 60/799,921, filed May 12, 2006, the disclosure of which is incorporated herein by reference in its entirety.

BACKGROUND OF THE INVENTION

The present invention relates to color matching and, more specifically, to a computerized method of color matching transparent or semitransparent wood stains.

Stains are typically semitransparent solutions or suspensions of coloring matter (such as dyes or pigments or both) in a vehicle, designed to color a surface by penetration without hiding it or leaving a continuous film. In contrast, paints are opaque solutions or suspensions of coloring matter in a vehicle, designed to hide or cover a surface with an opaque film. Computerized color matching techniques using spectrophotometers are routinely used to color match paints. Heretofore, computerized color matching techniques using spectrophotometers have required the use of a selected wood substrate for color matching purposes as disclosed in US patent application 20040131756, published on Jul. 8, 2004. Using selected wood substrates adds on expense, and requires a selection step. Alternatively, semitransparent stains are conventionally color matched using a trial-by-error method. In such a trial-by-error method, a colorist inspects the color of the stain standard and then guesses the pigments in a library and relative concentrations necessary to provide a color matching stain. A stain is then prepared based on the pigment and concentration guesses. The stain is applied to a substrate and then the stained substrate is compared to the stain standard. If the visual inspection indicates that the stain standard and the stained substrate do not match, the colorist guesses at the amount of pigments to add to the stain and the new stain is applied to the substrate. These steps are repeated until the colorist determines that there is a color match. As can be appreciated, such a trial-by-error method is tedious and relies upon the skill of the colorist for its effectiveness. Accordingly, there is a need in the art for a simpler computerized method of color matching semitransparent stains. The present invention is directed to such a method.

SUMMARY OF THE INVENTION

In accordance with the present invention, a method is provided for producing a wood stain for a wood substrate, wherein the wood stain provides the wood substrate with a color that matches the color of a target object. The method includes the steps of providing a spectrophotometer, providing a plurality of different colorants, wherein none of the colorants are a white colorant or a black and white masstone, providing a vehicle for producing transparent or semitransparent wood stain and providing at least one database containing spectral data for the colorants as applied to a paper substrate.

Reflectance measurements of the target object are obtained using the spectrophotometer. Calculations are performed to determine the quantities of at least one group of the colorants required to produce a transparent or semitransparent wood stain from the vehicle, wherein when the semitransparent wood stain is applied to the paper substrate, the stained portion will have a color that matches the target object. The calculations are performed using the spectral data of the colorants and the reflectance measurements of the target object. The transparent or semitransparent stain is produced from the vehicle and the at least one group of colorants. A portion of the paper substrate is stained with the semitransparent wood stain and reflectance measurements of the stained portion of the paper substrate are obtained using the spectrophotometer. A determination is made whether the color of the stained portion of the paper substrate is within a certain color tolerance of the color of the target object. The determination is made using the reflectance measurements of the target object and the reflectance measurements of the stained portion of the paper substrate.

DETAILED DESCRIPTION OF THE PREFERRED EMBODIMENTS

The method of the present invention avoids the necessity to have high skill expert colorists for wood stain color matching as the color matching is provided by color matching software of the spectrophotometer and so avoiding any subjectivity in color matching. The method will speed up enormously color matching activity decreasing the probability to make errors due to difference in color perception by human eye. Moreover, by using an automatic tinting machine for color dispensing, wood stain preparation is much quicker and accurate than manual stain preparation. One of the advantage of this method is to make spectral data color file preparation much easier than when using a wood substrate since the wood stains application is performed directly on a paper substrate. Application of the wood stain can be done by dipping of the substrate into the stain, or any other staining method such as spraying or painting. For spectral data color file preparation, wood substrates are never used to generate color data file and so only a single set of color data file is generated for each group of colorants. The colorist need not be concerned about selecting a particular wood for a substrate, thus making the color matching process faster. Moreover, in case the target object to be matched is in the form of a liquid sample, standard white test charts can be used and the stain is suitably applied by dipping onto the paper chart and reflectance measurements are performed on such substrates. This makes the process much quicker than apply stains onto wood substrates.

As used herein, the term "wood stain" shall mean a semitransparent solution or suspension of coloring matter (such as dyes or pigments or both) in a vehicle (binder and thinner), designed to color a piece of wood by penetration without hiding it or leaving a continuous film. Wood stains have low solids contents relative to paint, i.e., frequently less than 20 percent by weight solids.

Wood stains can be oil-based or water-based. Oil-based wood stains generally comprise one or more pigments, a binder such as an alkyd resin containing a drier, and organic solvents such as mineral spirits, VMP naphtha, kerosene, xylene, toluene or a mixture of these. In contrast, water-based wood stains have waterborne binders such as acrylic emulsions and water dilutable alkyds.

As used herein, the term "vehicle" shall mean a binder and one or more thinners and optionally other ingredients (excluding colorants) used to form wood stains.

As used herein, "colorant" shall mean a substance that imparts color to another material or mixture. Colorants can be either dyes or pigments (organic or inorganic). Pigments are insoluble in the vehicle, whereas dyes are soluble in the vehicle. Inorganic pigments include metal oxides such as the oxides of iron, titanium, zinc, cobalt, and chrome. Earth pigments may utilize mineral pigments obtained from clay. Various forms of carbon may be used for black pigments. Organic pigments are insoluble in the vehicle and are derived from natural or synthetic materials, and include phthalocyanine, lithos, toluidine, and para red. Organic pigments may be employed in a precipitated form as a lake. Dyes are organic materials and include acid dyes, such as azo, diazo and triarylmethane dyes, and basic dyes, such as aniline dyes.

Pigment-based colorants are often provided in the form of tinting concentrates comprising highly concentrated levels of color pigment dispersed into a vehicle. The amount of color pigment used in a colorant is typically from about 5 weight percent to about 70 weight percent, depending on the type of color pigment.

As used herein the term "chromatic colorant" shall mean a colorant that is not black, white or gray.

The present invention is directed to a method of color matching wood stains. More specifically, the present invention is directed to a method of producing a wood stain that when applied to a wood substrate will have the same or substantially the same color as a target object, taking into account clear topcoats or other finishes on the target object and/or the desired object. The method of the present invention may be used for both oil-based and water-based wood stains.

The method utilizes a spectrophotometer, such as a single angle spectrophotometer connected to a computer, such as a personal computer with a central processing unit. As will be described more fully below, the color matching software program includes a plurality of databases containing spectral data for colorants applied to a paper substrate. The color matching software program also contains one or more formula(s) for wood stain composition(s) (ex colorants) describing the required proportions of vehicle and other additives.

In use, the spectrophotometer is used in conjunction with a light analyzer, as disclosed in US application 20040131756, the disclosure of which is incorporated herein by reference in its entirety. The light analyzer also receives reference light from the light source, which is used to correct for variations in the intensity of the light source. The light analyzer includes a device for separating light into its component wavelengths, such as a diffraction grading or a prism, and an array of detectors to measure the intensities of the different wavelengths. Signals from the detector array are multiplexed and fed to a data processor (not shown), which produces digital signals that are conveyed to the personal computer.

A commercially-available single angle spectrophotometer that may be used in the present invention is the ColorEye 7000 color spectrophotometer sold by Gretag Macbeth.

The present invention utilizes a collection or library of different colorants. The colorant library includes a black colorant and a plurality of chromatic colorants. As will be described more fully below, the white colorant is used to determine the spectral characteristics of the other colorants, but the white colorant is not used to formulate the batch wood stain that is being produced to match a target object. In one embodiment of the present invention, the library of colorants comprises a variety of different colorants, including the black colorant.

The colorist calls up a wood stain formula (ex colorants) and enters the amount of batch wood stain that is desired into the color matching software program. The colorist then instructs the color matching software program to access the spectral data stored in the database for the paper substrate when the color matching software program performs the color matching calculations set forth below. The called-up wood stain formula (ex colorants) together with the colorants (and amounts thereof) calculated by the color matching software program are hereinafter collectively referred to as the batch wood stain formula.

Reflectance readings of the target object are then made using the spectrophotometer. Reflectance readings of the target object at four different locations are made. Two readings are made in two different light wood areas, e.g. sapwood areas, and two readings are made in two different darker wood areas, e.g. heartwood areas. Once again, readings are not made in knot areas or other areas containing defects. Each reading comprises a plurality of reflectance measurements made at 10 to 20 nanometer intervals along the visible light spectrum. The reflectance measurements of the four readings at each wavelength interval are averaged to produce average reflectance measurements.

The amount of the colorants that must be added to provide the batch wood stain with a color falling within the color tolerance value is determined based on mathematical calculations run by the color matching software program in the computer.

The mathematical procedure utilized to calculate the amount of the colorants to be added is well known in the art. A particularly useful procedure is that described in Eugene Allen's article in the Journal of the Optical Society of America, Volume 64, Number 7, July 1974 pages 991 to 993 the teaching of which is hereby incorporated by reference. A procedure based on Eugene Allen's method (similar to the one used herein) is described in U.S. Pat. No. 4,887,217 to Sherman et al., which is hereby incorporated by reference in its entirety. For a colorant having a given concentration, absorption coefficient and scattering coefficient, this procedure provides a determination of the amount of said colorant which must be added.

In a preferred application of the Eugene Allen color matching procedure, a mathematical technique is first applied to the batch wood stain in a prediction stage to determine, by an iterative process, the quantities of the colorants that must be added to the batch wood stain to theoretically match the target object. In a correction stage, the mathematical technique is again applied in an iterative process to determine the amount (if any) of the colorants necessary to move from the color of the produced batch wood stain to the desired color of the target object.

In the color matching procedure of the present invention, 3 or 4 colorant formulas are typically produced. If, however, the target object has a difficult to match color, such as a violet color, a very saturated dark color, or a highly chromatic color, a 5 colorant formula may be specified. Importantly, the white colorant is not used in the color matching. The black colorant may or may not be used in the color matching, depending on the color of the target object.

The color matching software program runs the foregoing equations for all four-colorant combinations of the colorants in the colorant library, excluding the white colorant and also preferably excluding the black colorant (depending on the color of the target object). Therefore, the color matching software program produces a number of different colorant formulations, with the white colorant (and also preferably the black colorant) being absent from each formulation. One of the colorant formulations is selected. This selection can be based on lowest cost, least metameric, or another reason.

Using the batch wood stain formula in the computer with the calculated amount of colorants required by the selected colorant formulation, a batch of wood stain is produced. The wood stain batch is applied to the paper substrate. If the target object is determined to have a clear topcoat, a clear top coat is applied to the paper substrate, over the region stained with the wood stain batch. Preferably, the paper substrate is allowed to dry.

Based on the average reflectance measurements from the stained portion of the paper substrate, a determination is made whether the color of the stained portion of the paper substrate is close enough to the target object. If the color of the stained paper substrate is not close enough to the color of the target object, the steps of (1)-(7) can then be repeated in the correction stage to re-determine the amount of the colorants needed to produce a second batch of the wood stain having a color that matches the color of the target object.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

Exemplary Materials, Methods And Alternative Methods

A. Materials

Following materials are been used:

At least one set of selected concentrated transparent or semitransparent stains

A target object which colour has to be matched by use of this automatic wood colour method; target object can be provided by:
1. a liquid transparent or semitransparent stain;
2. a stained wood surface.

Thinners (solvents or water) for the preparation of a plurality of colorant-thinner mixtures with different concentration necessary to prepare spectral colour file Spectrophotometer designed to measure diffuse or specular reflectance Colour matching software for the spectrophotometer Standard test charts (b/w Leneta test chart 5DX have been used). Any other type of standard test charts or absorbing substrate could also work for the purpose.

One automatic dispensing tinting machine through which liquid transparent or semitransparent colorants are dispensed according to the formulation generated by reflectance measurement based on spectral data file. The machine has different canisters each one containing a single concentrate colorant and a system of pipes and volumetric pumps through which colorants are dispensed simultaneously into a holder where the stain sample is prepared.

B. Methods

The method for automatic wood colour matching provides the following steps:

1 Select one specific group of transparent or semitransparent colorants that has to be used to produce a transparent or semitransparent wood colour stain sample to match the colour of a target object;

2 create a single spectral data file for the selected group of colorants that is specific for this group;

3 to perform reflectance measurements of the colour of a target object by reading one area that is recognized to be significant for the colour matching.

4 produce a stain formulation on the result of the reflectance measurement based on spectral data file. This stain is provided by a tinting machine which dispense each single liquid colorant according to the formulation given by the colour matching software with an accuracy of 0.02 cc;

5 apply this stain onto paper substrate. Application method of the stain could be by dipping, spray or wiping 6 to measure the difference between the achieved colour and the target object. If this difference is within a certain tolerance the colour of the target object has been successfully matched otherwise is necessary to re-iterate process from step 4 to 6 providing reflectance measurements based on colour correction option of the colour matching software.

As example (not limitative for the method and for the claims) is described for a set of water based stains manufactured by Arch Sayerlack Coatings Italy. Each single stain can be made by one single type of dye or a blend of different dyes The same method is applicable to solvent based stains or any other type of transparent or semitransparent stains.

In this example the thinner is used for producing a plurality of binary colorant-thinner mixtures is tap water.

Spectral Data Colour File Preparation

Spectral data file is specific of this selected type of stain and its preparation is described below.

A plurality of binary colorant-water mixtures were prepared with various dyes percentages of the colorants in each mixture. Selected colorants were: yellow-bordeaux-orange-brown-yellow-red-black.

For each colorant a minimum of 8 mixtures are suitably prepared as follows (300 grams each mixture):

0.2% colorant+99.8% water
0.3% colorant+99.7% water
0.5% colorant+99.5% water
0.7% colorant+99.3% water
1.0% colorant+99.0% water
2.0% colorant+98.0% water
4.0% colorant+96.0% water
6.0% colorant+94.0% water Standard test charts have been dipped into each mixture for at least 10 seconds and then dried at room temperature for at least 30 minutes.

Once stained test charts are dried, reflectance measurements are performed on each test chart by using the spectrophotometer (small area and multiple reading option have been selected for the spectrophotometer and the final reflectance is given by the average value of three contemporary readings generated by this multiple reading option); data are stored into a spectral data file that is specific for the group of colorant is used.

Colour Matching of a Target Object

Once data file has been created and stored, in order to verify spectrophotometer calibration, reflectance measurements are performed on each stained test chart but reading the colour on different areas then the one used for the calibration and then providing a stain formulation that had to match with the known colorant concentration of the mixtures within a 5% error tolerance.

According to the type of target object the following methods are suitably used.

1) Target Object is a Liquid Transparent or Semitransparent Stain Sample.

In this case a standard test chart is dipped into the liquid stain to achieve a stained surface that is the target object to match. Reflectance measurement of the stained portion is provided to produce a stain formulation on the result of this reflectance measurement based on a specific spectral data file. This formulation is then applied onto a new test chart; if the difference between the target object and the new stained test chart (for which colour formulation has been provided by the spectrophotometer) is within a certain tolerance the process ends, otherwise the reflectance measurement is re-iterated until the difference between the colour of the last formulation provided by the software and the target object is within a certain tolerance.

2) Target Object is a Stained Wood Surface.

In this case reflectance measurement of the stained portion of the target object is provided to produce a stain formulation on the result of this reflectance measurement based on a specific colorant spectral data file. This formulation is then applied by applying it onto paper chart achieving a stained surface: if the difference between the target object and the new stained area (for which colour formulation has been provided by the spectrophotometer) is within a certain tolerance the process ends, otherwise the reflectance measurement is re-iterated until the difference between the colour of the last formulation provided by the software and the target object is within a certain tolerance.

C. Alternative Methods

1 Select one specific group of transparent or semitransparent colorants that is to be used to produce a transparent or semitransparent wood colour stain to match the colour of a target object 2 use of standard white test charts as substrate where colorant-thinner mixtures are applied in order to create a spectral data file for the selected group of colorants.

a. It's possible to use different types of white blotting paper with a certain density in order to achieve a uniform stain absorption on the chart surface or any other type of absorbing substrate. In fact the method is not limited to the use of standard white test chart. Any kind of absorbing substrate can work, preferably if the colour of the paper substrate is standardized within a certain tolerance.

b. For each colorant a minimum of 8 mixtures have been prepared. This is the preferred number of mixtures have to be prepared in order to create a spectral data file with high accuracy. A higher number of different mixtures can be prepared and this results in a higher accuracy achieving optimum results (usually given by a maximum of 10-12 mixtures)

c. Spectral data colour file is unique for a specific group of colorants. In case of target object is a stained wood surface, this file is called up by the colourist independently by the type of wood is used.

3 To perform reflectance measurements of the colour of a target object;

4 Produce a stain formulation on the result of the reflectance measurement based on the spectral data file created at step 2. This stain is provided by a tinting machine which dispense each single liquid colorant according to the formulation given by the colour matching software with an accuracy in the dispensed amount of 0.02 cc;

a. Preparation of stain formulation can be performed also manually by a human operator who, for each colorant indicated by the colour matching software in a certain amount, weights or dispenses by volume this quantity in order to achieve a liquid stain sample to be applied on the appropriate substrate. In this case time is much longer and accuracy much lower due to possible human errors in weight or volumetric dispensing.

5 Apply this stain on the appropriate substrate;

6 To perform reflectance measurements of the colour of the stained surface;

7 To measure the difference between this colour and the target object. If this difference is within a certain tolerance the colour of the target object has been successfully matched otherwise is necessary to re-iterate process providing reflectance measurements based on colour correction option of the colour matching software.

What is claimed is:

1. A method of producing a wood stain for a wood substrate, wherein the wood stain provides the wood substrate a color that matches the color of a target object, said method comprising the steps of: providing a spectrophotometer; providing a plurality of different colorants, wherein none of the colorants are a white colorant or a black and white masstone; providing a vehicle for producing transparent or semitransparent wood stain; providing at least one database containing spectral data for the colorants as applied to a paper substrate; obtaining reflectance measurements of the target object using the spectrophotometer; performing calculations to determine the quantities of at least one group of the colorants required to produce a transparent or semitransparent wood stain from the vehicle, wherein when the transparent or semitransparent wood stain is applied to the paper substrate to provide a stained portion, the stained portion will have a color that matches the target object, and wherein the calculations are performed using the spectral data of the colorants and the reflectance measurements of the target object; producing the transparent or semitransparent wood stain from the vehicle and the at least one group of colorants; staining a portion of the paper substrate with the transparent or semitransparent wood stain; obtaining reflectance measurements of the stained portion of the paper substrate using the spectrophotometer; and determining whether the color of the stained portion of the paper substrate is within a certain color tolerance of the color of the target object, wherein the determination is made using the reflectance measurements of the target object and the reflectance measurements of the stained portion of the paper substrate.

2. The method of claim 1, wherein if the color of the stained portion of the paper substrate is not within the certain color tolerance, the method comprises the following additional steps: performing additional calculations to determine quantities of the at least one group of the colorants required to produce a second semitransparent wood stain from the vehicle, wherein when the second semitransparent wood stain is applied to a second portion of the paper substrate, the second portion of the paper substrate will have a color that matches the target object, and wherein the additional calculations are performed using the spectral data of the colorants, the reflectance measurements of the target object and the reflectance measurements of the stained portion of the paper substrate; producing the second semitransparent wood stain from the vehicle and the at least one group of colorants; and staining a second portion of the paper substrate with the second semitransparent wood stain; obtaining reflectance measurements of the stained second portion of the paper substrate using the spectrophotometer; and determining whether the color of the stained second portion of the paper substrate is within a certain color tolerance of the color of the target object, wherein the determination is made using the reflectance measurements of the target object and the reflectance measurements of the stained second portion of the paper substrate.

3. The method of claim 2, wherein the target object is a stained piece of wood and wherein the reflectance measurements of the target object are average reflectance measurements, each of said average reflectance measurements being an average of localized reflectance measurements taken at a plurality of different locations on the target object.

4. The method of claim 3, wherein the localized reflectance measurements of the target object are made in at least one light wood area and in at least one dark wood area.

5. The method of claim 4, wherein the localized reflectance measurements of the target object are made in two light wood areas and in two dark wood areas.

6. The method of claim 1, wherein the target object is a stained piece of wood, and wherein the method further comprises the step of inspecting the target object to determine if it has a clear topcoat, and wherein if the target object is determined to have a clear topcoat, the method further comprises the steps of providing a clear topcoat and applying the topcoat to the stained portion of the paper substrate before obtaining the reflectance measurements of the stained portion of the paper substrate.

7. The method of claim 1, wherein the calculations are performed using a computer.

8. The method of claim 1, wherein the target object is a liquid transparent or semitransparent stain and wherein in the reflectance measurements of the target object are average reflectance measurements, each of said average reflectance measurements being an average of localized reflectance measurements taken at a plurality of different locations on the target object.

* * * * *

UNITED STATES PATENT AND TRADEMARK OFFICE
CERTIFICATE OF CORRECTION

PATENT NO. : 7,623,241 B2  Page 1 of 1
APPLICATION NO. : 11/787990
DATED : November 24, 2009
INVENTOR(S) : Maurizio Brini and Barbara Bartolomei It is certified that error appears in the above-identified patent and that said Letters Patent is hereby corrected as shown below:

On the cover page at item (73), please delete
"Arch Chemicals, Inc., Norwalk, CT (US)" and insert at (73) Assignee:

--Arch Sayerlack Coatings S.r.l., ITALY--

Signed and Sealed this
Sixth Day of September, 2011

David J. Kappos
*Director of the United States Patent and Trademark Office*